United States Patent [19]

Sabolich

[11] Patent Number: 5,219,365
[45] Date of Patent: Jun. 15, 1993

[54] PROSTHETIC FOOT

[75] Inventor: John A. Sabolich, Arcadia, Okla.

[73] Assignee: Sabolich, Inc., Oklahoma City, Okla.

[21] Appl. No.: 935,683

[22] Filed: Aug. 26, 1992

Related U.S. Application Data

[63] Continuation of Ser. No. 815,909, Dec. 30, 1991, abandoned, which is a continuation of Ser. No. 689,412, Apr. 22, 1991, abandoned, which is a continuation of Ser. No. 375,369, Jun. 29, 1989, abandoned, which is a continuation-in-part of Ser. No. 324,052, Mar. 20, 1989, abandoned, which is a continuation-in-part of Ser. No. 217,758, Jul. 11, 1988, abandoned, which is a continuation-in-part of Ser. No. 176,300, Mar. 31, 1988, abandoned.

[51] Int. Cl.$^5$ ................................ A61F 2/66
[52] U.S. Cl. ...................................... 623/55; 623/53
[58] Field of Search ......................... 623/53-55

[56] References Cited

U.S. PATENT DOCUMENTS

| | | |
|---|---|---|
| 2,075,583 | 3/1937 | Lange . |
| 2,440,075 | 4/1948 | Campbell ............................. 623/50 |
| 3,480,972 | 12/1969 | Prahl . |
| 3,484,871 | 12/1969 | Orange . |
| 3,833,941 | 9/1974 | Wagner . |
| 4,089,072 | 5/1978 | Glabiszewski . |
| 4,328,594 | 5/1982 | Campbell et al. ..................... 623/55 |
| 4,461,045 | 7/1984 | Shorter et al. . |
| 4,463,459 | 8/1984 | Shorter et al. . |
| 4,547,913 | 10/1985 | Phillips ............................... 623/27 |
| 4,645,509 | 2/1987 | Poggi et al. ......................... 623/55 |
| 4,721,510 | 1/1988 | Cooper et al. ....................... 623/55 |

FOREIGN PATENT DOCUMENTS

| | | |
|---|---|---|
| 0234886 | 9/1987 | European Pat. Off. . |
| 295807 | 12/1916 | Fed. Rep. of Germany . |
| 330285 | 12/1920 | Fed. Rep. of Germany . |
| 883321 | 7/1953 | Fed. Rep. of Germany . |
| 8800815 | 2/1988 | PCT Int'l Appl. . |
| 778732 | 12/1980 | U.S.S.R. . |
| 1371996 | 10/1974 | United Kingdom . |
| 2070439 | 9/1981 | United Kingdom . |
| 2084025 | 4/1982 | United Kingdom . |
| 2110936 | 6/1983 | United Kingdom . |

OTHER PUBLICATIONS

Otto Bock brochure, Orthopedic Industry, Inc. 1986.
Brochure, "Carbon Copy II," Ohio Willow Wood Company 1986.
Alignment and Installation Manual for Seattle Foot TM, Model and Instrument Development, Inc. 1986.
Brochure, Sten TM foot, Kingsley Manufacturing Co, Sep. 1985.
"Seattle Foot TM Steps" Newsletter, Model+Instrument Development, Summer 1987.
"Seattle Foot TM Steps" Newsletter, Fall 1987.

*Primary Examiner*—Richard J. Apley
*Assistant Examiner*—Joe Cheng
*Attorney, Agent, or Firm*—Dunlap, Codding & Lee

[57] ABSTRACT

The present invention provides a prosthetic foot comprising an integrally formed, flexible keel preferably in a cosmetic covering. The keel has a forefoot portion and a heel portion joined by an ankle portion. The inferior aspect of the ankle portion defines an arch which expands in response to a load, and the superior aspect of the ankle portion forms a platform which engages a conventional leg assembly. The forefoot portion is contoured, thicker on the medial side than on the lateral side, which shifts the midline of weight distribution in the forefoot portion medially. This provides a more natural alignment of the foot during the gait cycle. The toe end of the forefoot portion is biased along the natural toe break line. The posterior aspect of the ankle portion defines a concavity under the platform which is continuous with the superior aspect of the heel portion. A horizontal slot continuous with the concavity extends from the posterior aspect of the ankle portion between the platform and the arch. The anterior end of the slot is enlarged and rounded. Thus, the length of the heel is increased. This enhances the flexibility and shock absorbing capacity of the keel. The cosmetic covering is solid except for a cavity under the arch.

24 Claims, 5 Drawing Sheets

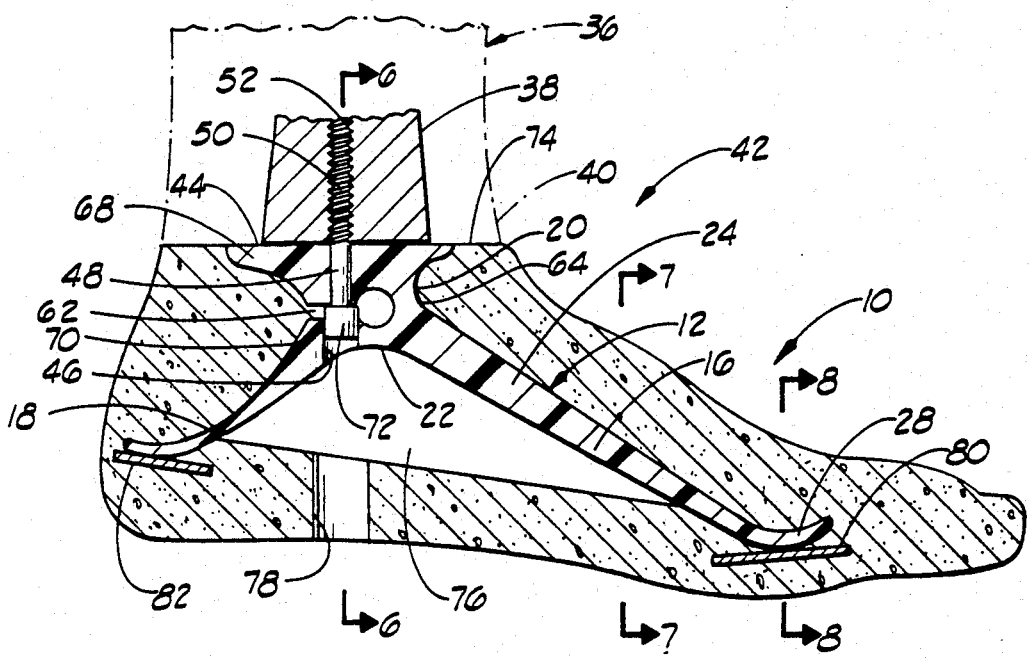
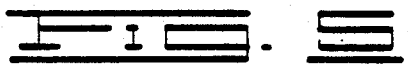
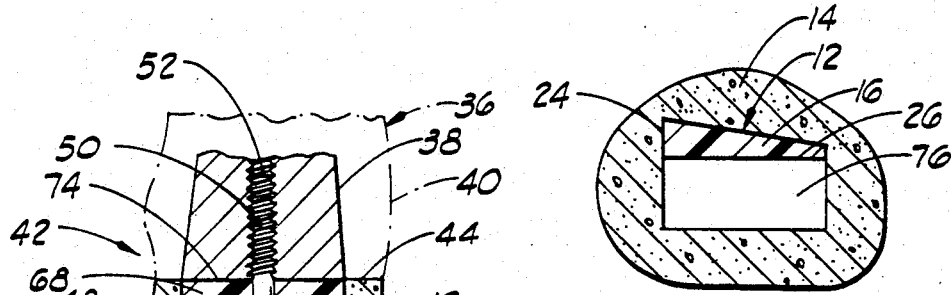
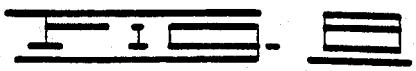

PROSTHETIC FOOT

This is a continuation of pending prior application Ser. No. 07/815,909, entitled "Prosthetic Foot", filed on Dec. 30, 1991, now abandoned, which was a continuation of prior application Ser. No. 07/689,412, entitled "Prosthetic Foot", filed on Apr. 22, 1991, now abandoned, which was a continuation of application Ser. No. 07/375,369, entitled "Prosthetic Foot", filed on Jun. 29, 1989, now abandoned, which was a continuation-in-part of application Ser. No. 07/324,052, filed Mar. 20, 1989, entitled "Prosthetic Foot", now abandoned, which was a continuation-in-part of application Ser. No. 217,758, entitled "Prosthetic Foot", filed Jul. 11, 1988, now abandoned, which was a continuation-in-part of application Ser. No. 176,300, also entitled "Prosthetic Foot", filed Mar. 31, 1988, and now abandoned.

FIELD OF THE INVENTION

The present invention relates generally to prosthetic devices and in particular to prosthetic feet.

BACKGROUND OF THE INVENTION

Since the first peg leg, prosthetists have been striving for a satisfactory substitute for the human foot, which is an intricate structure of over fifty bones and muscles. In an attempt to imitate the functional dynamics of the human foot, prosthetists designed artificial feet which structurally were almost as complicated as the human counterpart. These devices typically comprised numerous wooden, rubber and metal components, which made them cumbersome to wear. Moreover, because of their construction, they were expensive to manufacture and required considerable maintenance and repair.

It is only in recent years that those skilled in prosthetics have begun to use simpler designs which achieve flexibility through the use of resilient materials. These so-called "energy storing" feet absorb some of the impact with each step and then release this energy as the foot is lifted.

Several "energy-storing" feet are known. For example, U.S. Pat. No. 4,721,510 described a foot comprising a rigid arched keel clamped to the top of a longer flexible arched stiffener. The stiffener has a heel and a toe portion, and the keel also has a heel and a toe portion, each of which is spaced a distance above the corresponding portion of the stiffener. The keel and stiffener are attached to a thickened instep region in the cosmesis, which is hollow. In operation, when the toe and heel portions of the stiffener are deflected, they contact the overlying portions of the keel, thereby transmitting the ground reaction to the keel. Thus, the keel and stiffener components of this foot interact as a leaf spring.

A prosthetic foot with a monolithic cantilever spring keel is shown in U.S. Pat. No. 4,645,509. The keel is C-shaped, the back of the "C" forming a heel transition portion and the bottom of the "C" extending a length into a forefoot portion. Shock absorption results from the vertical compression of the curved heel transition portion. In an alternate embodiment, the keel is provided with an integral heel spur which is a short spike extending downwardly from the back of the heel transition portion. The state purpose of the spur is to absorb energy and provide rebound at heel strike.

A combination foot and leg prothesis is the subject of U.S. Pat. No. 4,547,913. The forefoot portion and the leg portion are integrally formed of a single flat strip of flexible material with a bend at the level of the ankle. A second and separate strip is riveted to the posterior aspect of the first portion to form the heel of the prosthesis. In most of the embodiments shown, the heel portion is C-shaped with the back of the "C" facing posteriorly. Thus, energy absorption occurs by compression of the sharp bend in the heel member and by flexion of the forefoot portion.

Finally, Russian Inventor's Certificate No. 778,732 discloses a foot comprising an integrally formed shock absorber housed in a shell which is filled with foam. The shock absorber has a lower branch, which repeats the curvature of the arch of the human foot, and an upper branch which slidably contacts the upper surface of the lower branch in the area of the metatarso-phalangeal joints. The upper branch is supported over the lower branch by a curved transition portion in the heel area. When a load is applied to the foot, the transition portion is compressed vertically, and the upper branch slides anteriorly upon the lower branch. Thus, the upper and lower branches of the shock absorber function as a leaf spring.

These feet generally are lighter weight and provide a more natural stride than the earlier more complicated mechanical prostheses. However, while these known devices represent advances in the art, problems have remained with their use.

One disadvantage to most known prosthetic feet results from the symmetrical thickness of the forefoot portions of the structural components of most of these devices. When walking casually on a foot with a symmetrical keel, an individual usually will toe the foot out slightly. This looks more natural and gives lateral stability. However, when walking vigorously and when running, an individual wearing such a device will want to turn the foot so that at each toe-off the end of the forefoot is aligned with the direction in which he or she is running. This is necessary to achieve a symmetrically resistant toe-off and thus enjoy the maximum spring from rebound of the forefoot. To turn the foot, the wearer must reposition the hip. This maneuver must be repeated with each stride and consumes a great deal of energy.

In another aspect, most known prosthetic feet lack the flexibility in the heel required for balanced absorption of purely vertical impacts, which occur frequently during athletic activities. For shock absorption, most of these devices depend primarily on vertical compression of a sharp bend, as a C-shaped heel portion. The rebound resulting from this compression, particularly in response to a substantially vertical impact, often throws the wearer backwards. Moreover, a configuration which depends for flexibility upon compression of a sharp bend is more susceptible to breakage.

SUMMARY OF THE INVENTION

The present invention comprises a prosthetic foot having as its primary structural element a single keel with a forefoot portion, an ankle portion and a heel portion. The keel is flexible and preferably is integrally formed of a hardened acetal copolymer. The inferior aspect of the ankle portion defines an arch which expands in response to a load.

In the preferred embodiment, the forefoot portion is contoured so that the medial side is thicker than the lateral side, and the to end of the forefoot is biased along the natural toe break line. Also, the upper portion of the ankle portion defines a platform, and the posterior aspect of the ankle portion under the platform and the superior aspect of the heel portion continuous therewith define a concavity.

The ankle portion of the keel may be provided with a vertical throughbore for connecting the foot to any of several commercially available leg assemblies in a known manner. Due to the particular design of the present foot, the apex of the keel's arch is anterior to the central axis of the pylon of most leg assemblies. To adjust for this, the central axis of the bore is posterior to the apex of the arch of the keel.

Usually, it will be desirable to cover the keel with a flexible cosmetic covering. The preferred covering of this foot is solid except for a cavity disposed under the ankle portion of the keel and extending a distance under the heel and forefoot portions as well. To prevent damage to the inside of the cosmetic covering, the ends of the forefoot and heel portions of the keel may be provided with bumpers.

A prosthesis constructed in accordance with the present invention overcomes the aforementioned problems common in prior art devices. The strength and dynamics of this prosthesis are derived mainly form the basic arched configuration of the keel. The arch has long been recognized as the strongest architectural shape. The inherent strength of the arched design permits the keel of the foot to be thinner, and thus lighter and more flexible.

The arch operating in concert with the uniquely shaped heel and forefoot portions provides balanced vertical shock absorption, most appreciated in running and jumping and the more strenuous athletic movements. The concavity formed at the point where the heel portion joins the ankle portion, which preferably is combined with the horizontal slot extending into the ankle portion, the length and thus the flexibility of the heel and ankle portions are increased. Yet, the entire keel fits nicely inside a naturally shaped cosmesis.

The forefoot portion of a prosthesis constructed in accordance with this invention will flex as much as 40 to 60 degrees. This configuration also increases the medio-lateral flexibility contributing to eversion and inversion of the foot.

In addition to being more flexible, the contoured forefoot with its biased toe end shifts medially the longitudinal midline of the wearer's weight distribution. This allows the wearer to walk vigorously and to run on the prosthesis without having to constantly reposition it and still enjoy the full rebound effect.

The unique design of the cosmetic covering provides the prosthesis with a pleasing appearance without obstructing the dynamic movements of the keel or adding unnecessarily to the weight of the foot.

The present invention further comprises a prosthetic foot having a flexible keel formed of an energy storing material and having a forefoot portion, a heel portion and an ankle portion therebetween. The inferior aspect of the ankle portion defines an arch, and the space under the arch is substantially unobstructed so that the arch can expand in response to a vertical load on the foot.

Still further, the present invention includes a lower limb prosthesis comprising a prosthetic foot as discussed above in combination with a leg assembly.

BRIEF DESCRIPTION OF THE DRAWINGS

FIG. 5 is a sectional view of the foot connected to a leg assembly.

FIG. 6 is a sectional view taken along line 6—6 of FIG. 5.

FIG. 7 is a sectional view taken along line 7—7 of FIG. 5.

FIG. 8 is a sectional view taken along line 8—8 of FIG. 5.

DETAILED DESCRIPTION OF THE PREFERRED EMBODIMENTS

Figure 1:
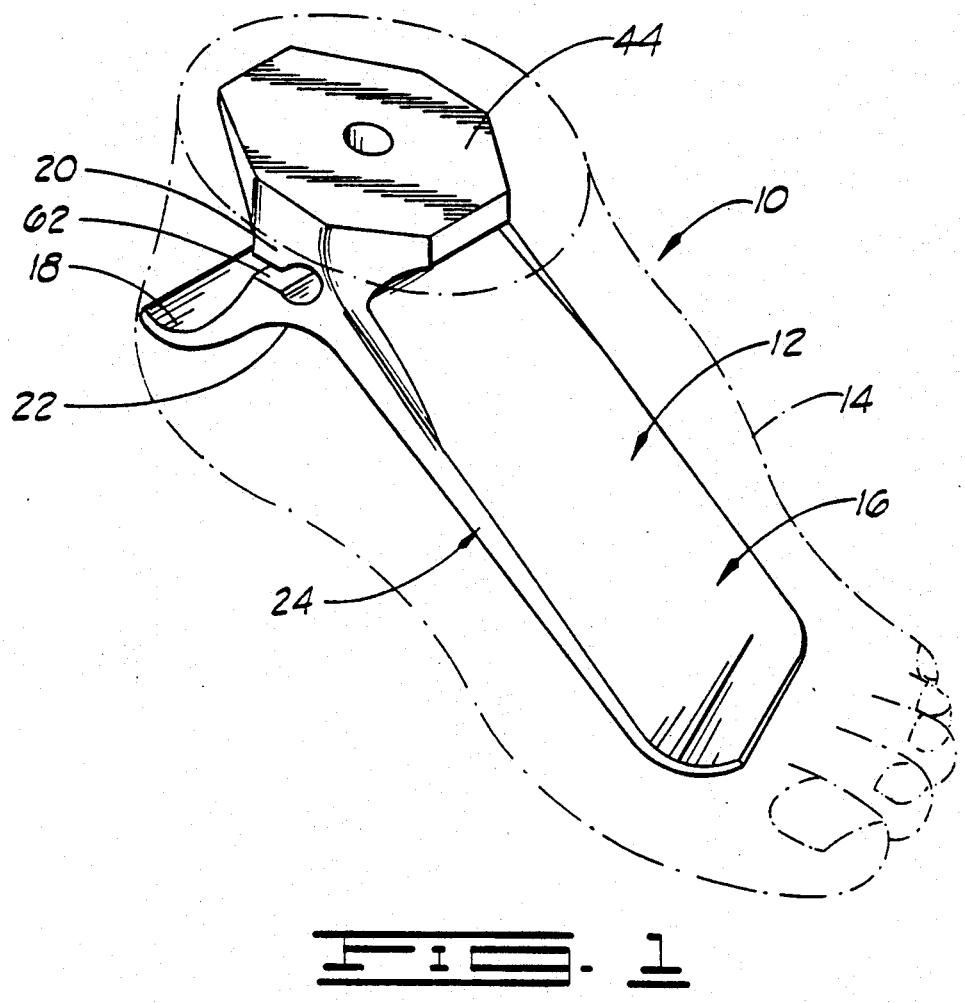
FIG. 1 is a perspective view of a prosthetic foot constructed in accordance with the present invention. The outer contours of the cosmetic covering are shown in phantom.

Referring now to the drawings in general and to FIG. 1 in particular, shown therein and designated by the general reference numeral 10 is a prosthetic foot constructed in accordance with the present invention. The foot 10 has as it primary structural element a single arched keel 12 which preferably is contained within a cosmetic covering 14 shown in dot-dash lines in FIGS. 1-4.

The keel 12 is integrally formed of a sturdy but resilient material. The density of the material and the degree of resiliency may vary and should be selected according to the physique and activity level of the intended wearer.

A preferred resilient material is a hardened acetal copolymer, such as that marketed under the brand name Celcon by the Celanese Corporation (Westlake, Ohio). This material has been found to be significantly more flexible than other materials, including acetal homopolymers. In order to achieve the maximum flexibility afforded by the unique configuration of the keel, the more flexible copolymer composition should be used.

The method of forming the keel may vary according to the resilient material selected. Where a solid copolymer acetal is used, the keel may be formed by known milling techniques. However, it will be appreciated that suitable polymer compositions are available in liquid form, and that these may be used to form the keel by injection molding procedures.

The resilient material is formed to provide a keel 12 having a forefoot portion 16 and a heel portion 18 continuous with an ankle portion 20 therebetween. The inferior aspect of the ankle portion 20 defines an arch 22. As shown best in FIGS. 2 and 3, the space 23 under the arch is substantially unobstructed so that arch can expand in response to a vertical load, as discussed more fully below. Most preferably, the keel 12 is integrally formed; that is, carved or molded from a single piece of flexible material.

Beginning about where it joins the ankle 20, the forefoot 16 is tapered; that is, it gradually lessens in thickness. The heel portion tapers similarly. This tapering provides increased flexibility.

The dimensions of the keel 12, including the heel height, may be varied to suit the wearer. Generally, a wider keel will provide better stability for heavier persons and those who enjoy strenuous physical activity. On the other hand, a smaller and narrower keel is best for children, and women may prefer an elevated heel which permits them to wear fashionable high heeled shoes. The arch 22 may be higher or lower to provide more or less flexibility. For example, an unusually heavy individual requires a flatter arch, a so-called "low profile" version. It also will be appreciated that a low profile keel may be necessary where the lower leg of the wearer is unusually long.

Attention now is directed to the shape of the forefoot portion 16 of the keel 12. It is known that in a normal gait cycle, the body moves generally forward along a straight line which is preferred to in the art as the line of progression. However, with each stride the forefoot is turned outwardly slightly, so that the longitudinal midline of the foot is at an angle to the line of progression. Typically, the foot turns out about 7 to 12 degrees from the line of progression.

The structure of the human foot is built accordingly. The heavier, larger bones on the medial side and the slanted toe break line formed by the toe joints support most of the weight toward the medial side and provide power at toe-off, while at the same time the lateral portion of the foot provides stability during walking. The prosthetic foot of this invention mimics the biomechanics of the human foot by providing the forefoot 16 of the keel 12 with an asymmetrical contour.

Figure 2:
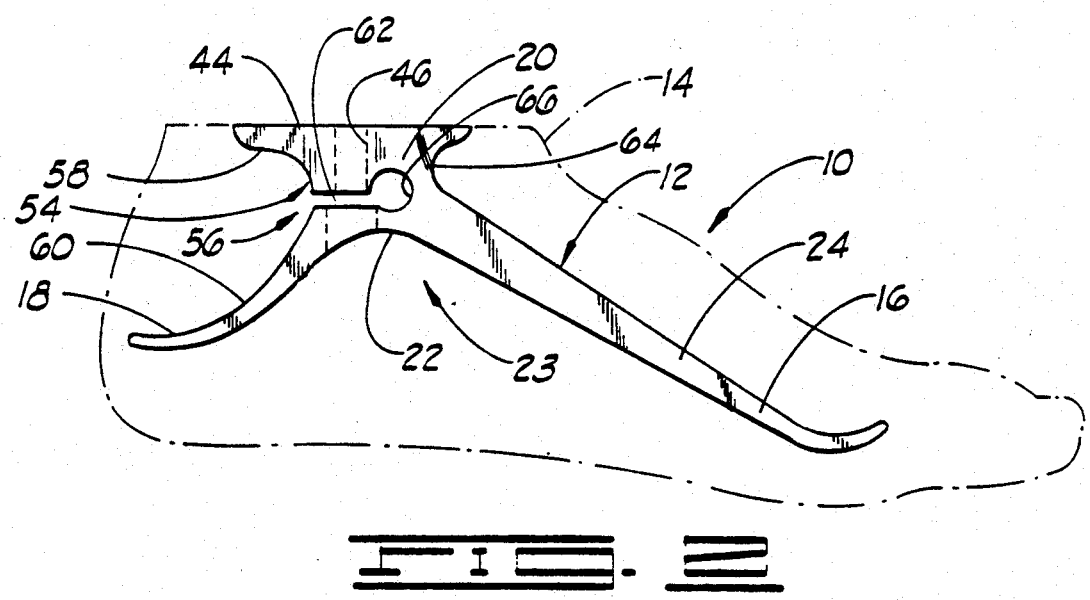
FIG. 2 is an elevation view of the medial side of the foot shown in FIG. 1.
Figure 3:
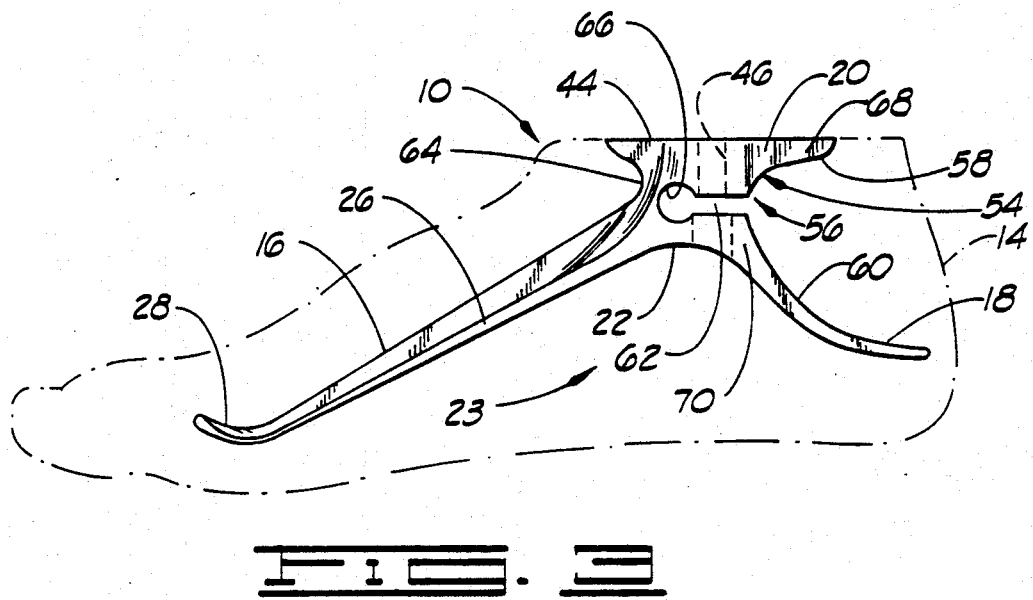
FIG. 3 is an elevation view of the lateral side of the foot shown in FIG. 1.
Figure 4:
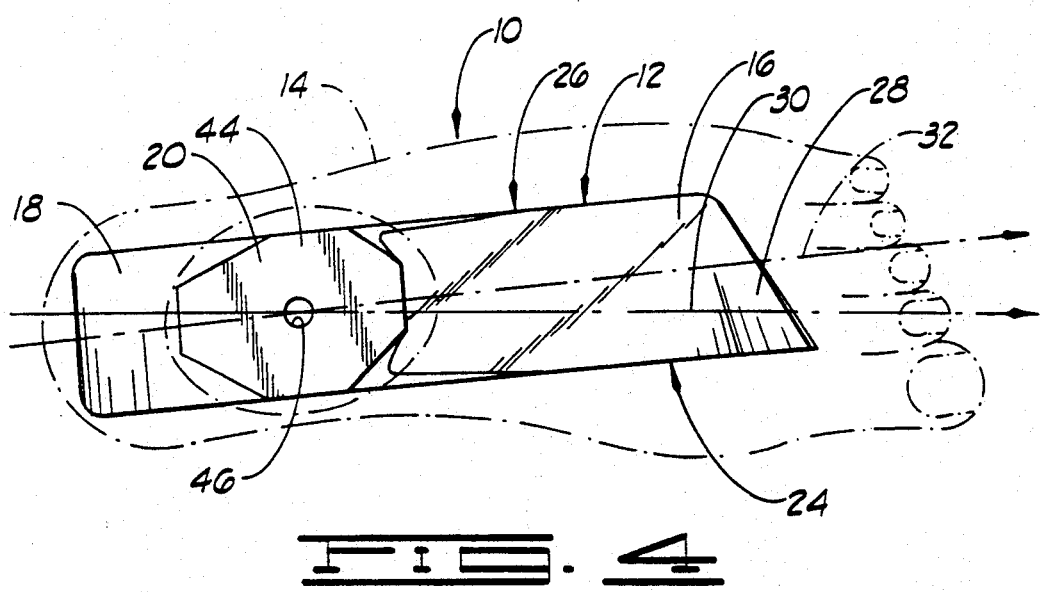
FIG. 4 is a plan view of the foot shown in FIG. 1.

Specifically, referring still to FIG. 1 and now also to FIGS. 2 through 4, the forefoot portion 16 preferably is contoured so that the medial side 24 (FIG. 2) is thicker than the lateral side 26 (FIG. 3). The effect of this contouring of the forefoot is illustrated in FIG. 4. The solid arrow 30 designates the longitudinal midline of weight distribution across the forefoot 16 at midstance. The broken arrow 32 designates the true longitudinal centerline of the forefoot 16. Thus, the load is shifted to the medial side of the forefoot 16. During the gait cycle, the midline of weight distribution 30 remains generally parallel to the line of progression, while the true longitudinal midline 32 of the foot is at a slight angle to the line of progression in a normal fashion.

With continuing reference to FIGS. 1 through 4, the toe end 28 preferably is biased so that the medial side 24 is longer than the lateral side 26. In this way, the toe end conforms to the line along which the toes in the natural foot flex relative to the forefoot, referred to as the toe break line. This biased toe end enhances the biomechanics of the prosthesis 10 by providing less resistance in the lateral aspect of the keel 12 at toe-off. The toe end 28 also may be upturned slightly. This will prevent tearing of the cosmetic covering 14, and also will provide a smoother toe-off.

All prosthetic feet must be attached in some manner to the end of the wearer's affected limb. This may be accomplished by using a variety of known leg components, including pylons (these form the lower leg), ankle and knee joints, and sockets. The components which combine to serve as the lower leg portion are referred to herein simply as a "leg assembly". A prosthetic foot in combination with a leg assembly is referred to herein as a "lower limb prosthesis".

Turning now to FIGS. 5 and 6, the foot 10 of the present invention is shown attached to a conventional leg assembly 36, which comprises a pylon 38 inside a cosmetic covering 40, to form a complete lower limb prosthesis 42. It will be understood that the foot 10 could be adapted for use with virtually any commercially available leg assembly.

The upper portion of the ankle portion 20 preferably defines a platform 44 (see also FIG. 1), which engages the inferior aspect of the leg assembly 36. The periphery of the platform 44, best seen in FIG. 4, may be shaped to fit within the ankle portion of the cosmetic covering 14.

For connecting the foot 10 to the leg assembly 36, the ankle portion 20 has a throughbore 46 through which a bolt 48 extends. The threaded end 500 of the bolt 48 threadedly engages the threaded bore 52 in the lower end of the pylon 38. As best seen in FIG. 5, the bore 46 should be positioned in the ankle portion 20 so that the central axis of the bore is disposed slightly posterior to the apex of the arch 22 in the keel 12.

Because of the flexibility of the foot, it may be desirable in some instances to provide the keel with an integrally formed pylon to form a complete lower limb prosthesis. This then can be covered cosmetically.

Returning now to FIGS. 2 and 3, the posterior aspect 54 of the ankle portion 20 defines a concavity 56 which is continuous with the inferior aspect 58 of the platform 44 and the superior aspect 60 of the heel portion 18. This configuration extends the length of the heel 18 and permits the heel to have a slender shape. Thus, the heel portion 18 is deformable along along its entire length. It will be appreciated that in some instances the throughbore 46 may intersect the concavity 56.

In the preferred embodiment, a horizontal slot 62 having a width is formed in the ankle portion 20 of the keel 12. The slot 62 is continuous with the concavity 56 of the posterior aspect of the ankle portion 20 and extends anteriorly therefrom towards the anterior aspect 64 of the ankle portion 20. The slot 62 generally is below and parallel to the platform 44 and above the arch 22 and intersects the throughbore 46.

The anterior end portion 66 of the slot 62 preferably is substantially circular in longitudinal cross section and ha a diameter greater than the width of the slot 62. The enlarged rounded end 66 of the slot stunts any tendency of the ankle portion 20 anterior to the slot to crack or break.

The slot 62 extends the entire width of the ankle portion 20. Thus, the slot 62 divides approximately the rear half of the ankle portion 20 into an upper segment 68 and a lower segment 70. The portion of the throughbore 46 which extends through the lower segment 70 is slightly larger than the portion which extends through the upper segment 68. In this way, the head 72 of the bolt 48 engages the upper segment 68, as best seen in FIGS. 5 and 6, so that the bolt will not interfere with the compression of the slot. Rather, the bolt head 72 can move in and out of the throughbore 46 in the lower segment 70 of the ankle portion 20.

It will be appreciated that when weight is placed on the foot 10, the slot 62 in the ankle portion 20 compresses at the same time that the arch 22 expands. Thus, the slot 62 in effect extends the length of the heel portion 18 and even further enhances the flexibility an the shock absorption capacity of the keel 12. This movement in the ankle portion 20 is similar to a slight dorsiflexion and plantarflexion and contributes to the anterior-posterior spring in the keel. In effect, the compression and release of the slot 62 mimic the natural movement of the ankle bones in the human foot.

With a heel portion formed in this manner, the keel can absorb a vertical shock and balance the impact therefrom between the heel 18 and forefoot 16. In other words, in response to a vertical load, the arch 22 expands evenly and without throwing or tipping the wearer anteriorly or posteriorly.

Although the cosmetic covering 14, shown best in FIGS. 5 through 8, is not necessary to the function of this prosthesis, in most instances it will be desirable. The covering 14 preferably consists of self-skinning polyurethane foam composition which when cured retains a soft, flesh-like consistency and color.

When formed in accordance with the present invention, the covering 14 is solid with an outer shape resembling a natural foot and an upper surface 74 at the level of the ankle and flush with the platform 44 of the keel 12 for close engagement with the inferior aspect of the leg assembly 36.

On the inside of the foot 10, the covering 14 conforms closely to the keel 12 except for a cavity 76 immediately beneath the arch 22 of the ankle portion 20. The cavity 76 extends a distance under the forefoot and heel portions 16 and 18 of the keel 12. The cavity 76 reduces the weight of the foot 10 and prevents the covering 14 from interfering with the flexibility of the keel 12.

The cavity 76 may be formed at the time the cosmetic covering 14 is formed by employing the sol-called "void wax" technique. A wedge of wax in the shape of the desired cavity is applied to the underside of the arch of the keel before the foam is applied. After the foam is applied and has set sufficiently, a bore 78 is drilled through the foot. Next, the wax is melted and drained out of the foot 10 through the bore 78. The bore 78 then permits the bolt 48 to be inserted into the keel 12, as described above.

With continuing reference to FIGS. 5 and 8, friction patches 80 and 82 may be placed immediately beneath the pressure points between the keel 12 and the cosmetic covering 14, namely under the toe end 28 of the forefoot portion 16 and beneath the heel portion 18. These patches most conveniently can be applied by gluing or the like, prior application of the cosmetic covering 14. The patches preferably are made of a sturdy fabric, such as polyethylene terephthalate cloth, laminated with a resin, such as urethane. The patches 80 and 82 will reduce wear on the covering and thus prolong the life of the foot 10.

Figure 9:
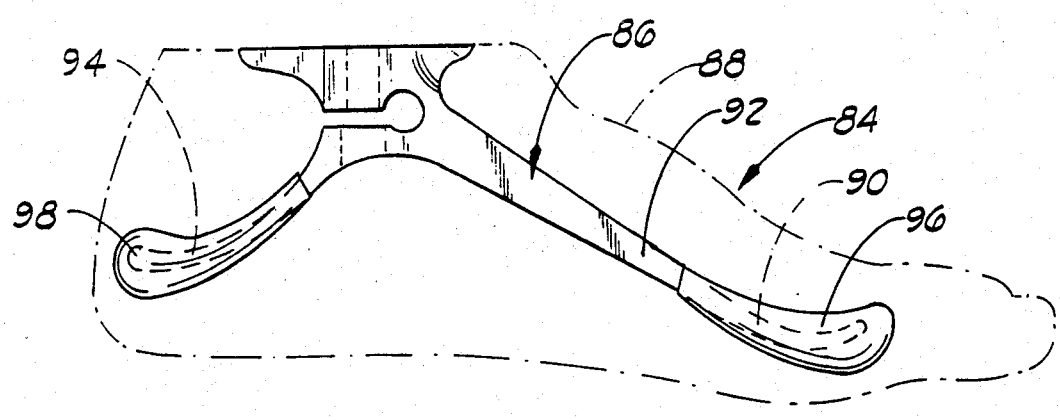
FIG. 9 is a side elevation view of another foot constructed in accordance with the present invention. In this embodiment the ends of the heel and forefoot portions of the keel are covered by protective bumpers.
Figure 10:
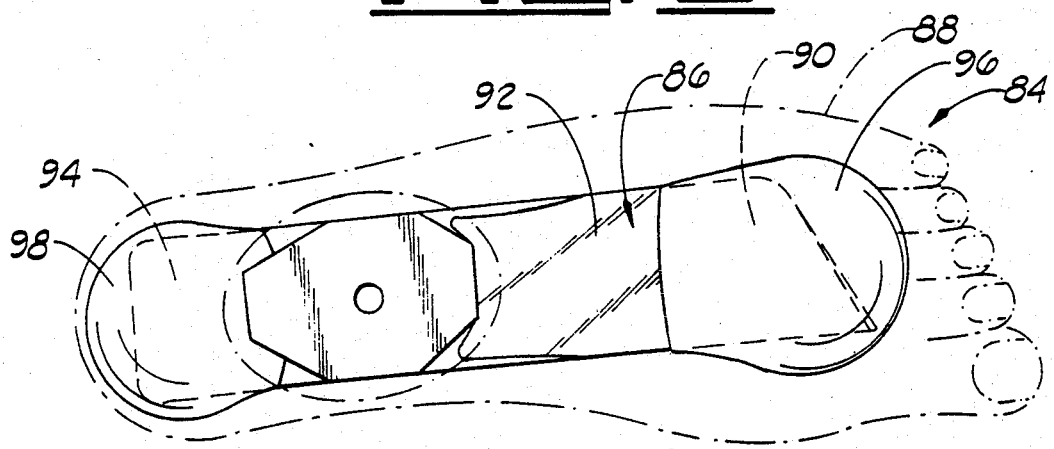
FIG. 10 is a top plan view of the foot shown in FIG. 8.

Shown in FIGS. 9 and 10 is another embodiment of the present invention. In this embodiment, the foot 84 comprises a keel 86 with a cosmetic covering 88 provided as described above. However, here each of the toe end 90 of the forefoot portion 92 and the heel portion 94 is provided with a flexible, bulbous tip or bumper 96 and 98, respectively. The bumpers 96 and 98 preferably are formed of a foam of greater density than the covering 88. By blunting the edges on the keel 12, the bumpers 96 and 98 reduce wear on the inside of the covering 88 without substantially affecting the flexibility or weight of the foot 84.

Figure 11A:
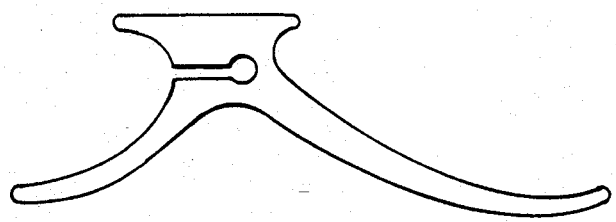
FIGS. 11A-11B illustrate schematically the vertical or lift dynamics of the foot of this invention.
Figure 11B:
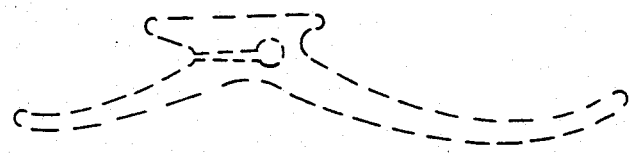

The lift or rebound characteristics of the foot of this invention during midstance are depicted schematically in FIGS. 11A and 11B. FIG. 11A depicts the keel in a relaxed or static position. In response to a load or sudden impact, the arch of the keel expands as shown in FIG. 11B, and absorbs the shock of impact. As the load is lifted, the arch of the keel springs back returning the keel to the shape shown in FIG. 11A. Because of the flexibility of the heel and the forefoot portion, the keel remains relatively level during this motion.

The balanced expansion of the keel in response to a sudden vertical impact, such as that caused by jumping and running, will be appreciated most by those who engage in strenuous sports and athletic activities. At this point, another important advantage of the construction of this foot will be apparent. This is the lateral to medial flexibility of the keel 12, which permits inversion and eversion of the prosthesis. This feature is most pronounced in the forefoot portion. Again, while this feature generally makes the prosthesis more comfortable for any wearer, it proves most advantageous to the athlete.

Figure 12A:
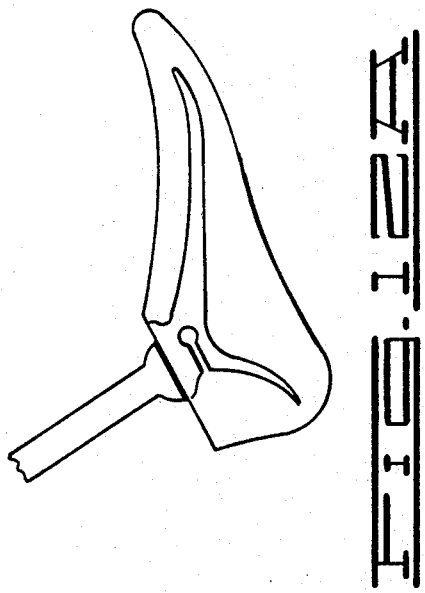
FIG. 12A-12E illustrate schematically the thrust dynamics of the foot during the stance phase of the gait cycle.

FIGS. 12A and through 12E depict the forward motion or thrust dynamics of the prosthetic foot of this invention during the stance phase of the gait cycle. FIG. 12A depicts heel strike, the first of the stance phases. This is the point immediately following the swing phase (not shown) at which the heel touches down and just prior to weight being shifted from the other foot to the prosthesis.

Figure 12B:
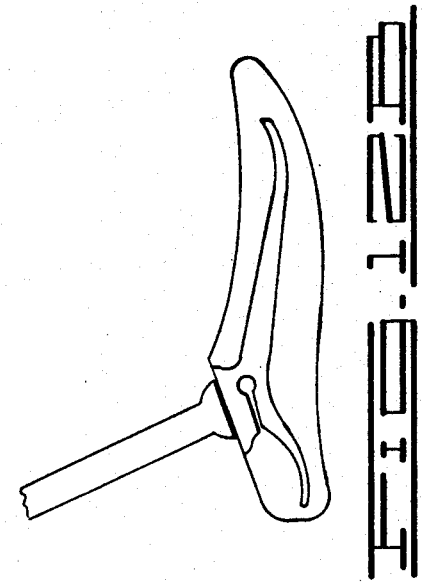

As weight shifts to the prosthesis, the heel portion of the keel flexes, as shown in FIG. 12B. By flexing at this point, the heel provides controlled movement of the foot from heel strike to midstance and eliminates the slapping effect sometimes experienced in prostheses with less resilience in the heel. Accordingly, the flexibility of the heel portion in this foot substitutes for the anterior muscles of the lower leg.

Figure 12C:
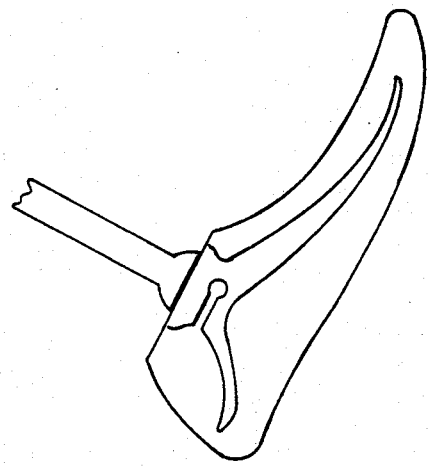

As the forefoot portion is brought down into midstance, shown in FIG. 12C, the tension in the heel is expressed as a thrust force propelling the foot forward towards midstance. Much of the impact of each stride is absorbed during midstance, which also is depicted in FIGS. 11A and 11B described previously.

Figure 12D:
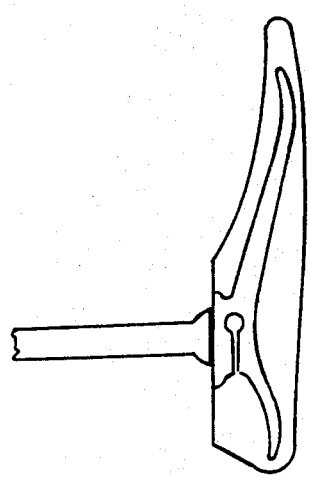

At the end of midstance and as the body of the wearer moves forward (FIG. 12D), the weight is lifted off the prosthesis. As the arch recoils, the wearer experiences a bounce or lift.

Figure 12E:
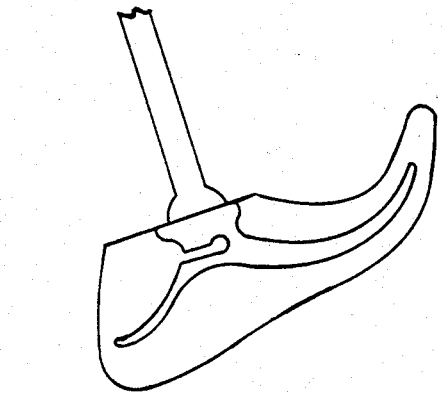

As the body continues to move forward and the opposite foot swings towards its next heel strike, the forefoot portion flexes, as shown in FIG. 12E. As the forefoot continues to flex, resistance increases preventing the wearer from moving forward too quickly. The release of the tension at push-off urges the foot up and away from the ground and propels the foot towards the next swing phase. The powerful spring action of the forefoot simulates the action of the posterior muscles in the lower leg.

Now it will be appreciated that the present invention provides a prosthetic foot having unique shock absorbing characteristics. Because of its shape and flexibility, all of the directional components of a single stride, from heel strike to toe-off are progressively absorbed by this foot as each portion of the keel is deformed and then rebounds to its original shape in a single, sustained and fluid movement. Similarly, purely vertical shocks are absorbed by balanced expansion of the arch. The positive energy produced by the rebound action actively participates in the mechanics of walking and running throughout the stance phase. Further, because of its simple construction, this lightweight and sturdy prosthesis can be produced economically and requires virtually no maintenance or repair.

Changes can be made in the nature, composition, operation and arrangement of the various elements, steps and procedures described herein without departing from the spirit and scope of the invention as defined in the following claims.

What is claimed is:

1. An energy storing prosthetic foot comprising a keel formed of an energy storing material, wherein the keel comprises a heel portion characterized by an elongate member, a forefoot portion characterized by an elongate member and an ankle portion, wherein the inferior aspects of the heel portion, the ankle portion and the forefoot portion define a resilient arch in the keel, wherein the keel is supported in the prosthetic foot so that the apex of the resilient arch is generally under the ankle portion of the prosthetic foot, wherein the keel is supported in the prosthetic foot so that the resilient arch is capable of expanding in response to a load on the prosthetic foot for storing energy and capable of contracting as the load is lifted to release the stored energy, wherein the keel is supported in the prosthetic foot so that in the assembled prosthetic foot the space under the resilient arch is substantially unobstructed, and wherein substantially all the energy storing capacity of the prosthetic foot resides in such expansion and contraction of the resilient arch of the keel.

2. The prosthetic foot of claim 1 wherein the forefoot portion, the heel portion and the ankle portion of the keel are integrally formed.

3. The prosthetic foot of claim 1 wherein the forefoot portion is contoured so that the medial side is thicker than the lateral side.

4. The prosthetic foot of claim 3 wherein the medial side of the forefoot portion is longer than the lateral side so that the end of the forefoot portion is biased along the natural toe break line.

5. The prosthetic foot of claim 1 wherein the medial side of the forefoot portion is longer than the lateral side so that the end of the forefoot portion is biased along the natural toe break line.

6. The prosthetic foot of claim 5 wherein the end of the forefoot portion and the end of the heel portion is covered by flexible bumpers.

7. The prosthetic foot of claim 1 wherein the superior surface of the ankle portion defines a platform, and wherein the posterior aspect of the ankle portion and the superior aspect of the heel portion continuous therewith define a concavity disposed a distance under the platform.

8. The prosthetic foot of claim 7 wherein the ankle portion of the keel is characterized as having a horizontal slot generally below and parallel to the platform and above the resilient arch and continuous with the concavity, wherein the horizontal slot extends a distance from the posterior aspect of the ankle portion towards the anterior aspect of the ankle portion to form an anterior end portion, and wherein the horizontal slot extends the width of the ankle portion.

9. The prosthetic foot of claim 8 wherein the anterior end portion of the horizontal slot is substantially circular in longitudinal cross section and has a diameter greater than the width of the slot.

10. The prosthetic foot of claim 8 wherein the ankle portion has a vertically aligned throughbore by which the prosthetic foot is connectable to a leg assembly, the throughbore having a central axis posterior to the apex of the resilient arch and intersecting the horizontal slot.

11. The prosthetic foot of claim 7 wherein the ankle portion has a vertically aligned throughbore by which the prosthetic foot is connected to a leg assembly, the throughbore having a central axis posterior to the apex of the resilient arch.

12. The prosthetic foot of claim 1 further comprising a cosmetic covering which is solid except for a cavity disposed under the resilient arch of the ankle portion and extending a distance under the forefoot portion and the heel portion.

13. A lower limb prosthesis comprising:

an energy storing foot comprising a keel formed of an energy storing material, wherein the keel comprises a heel portion characterized by an elongate member, a forefoot portion characterized by an elongate member and an ankle portion, wherein the inferior aspects of the heel portion, the ankle portion and the forefoot portion define a resilient arch in the keel, wherein the keel is supported in the foot so that the apex of the resilient arch is generally under the ankle portion of the foot, wherein the keel is supported in the foot so that the resilient arch is capable of expanding in response to a load on the foot for storing energy and to contract as the load is lifted to release the stored energy, wherein the keel is supported in the foot so that in the assembled foot the space under the resilient arch is substantially unobstructed, and wherein substantially all the energy storing capacity of the foot resides in such expansion and contraction of the resilient arch of the keel; a leg assembly; and means for connecting the leg assembly and the foot.

14. The lower limb prosthesis of claim 13 wherein the forefoot portion, the heel portion and the ankle portion of the keel are integrally formed.

15. The lower limb prosthesis of claim 13 wherein the forefoot portion of the keel is contoured so that the medial side is thicker than the lateral side.

16. The lower limb prosthesis of claim 15 wherein the medial side of the forefoot portion is longer than the lateral side so that the end of the forefoot portion is biased along the natural toe break line.

17. The lower limb prosthesis of claim 13 wherein the medial side of the forefoot portion is longer than the lateral side so that the end of the forefoot portion is biased along the natural toe break line.

18. The lower limb prosthesis of claim 17 wherein the end of the forefoot portion and the end of the heel portion are covered by flexible bumpers.

19. The lower limb prosthesis of claim 13 wherein the superior surface of the ankle portion defines a platform, and wherein the posterior aspect of the ankle portion and the superior aspect of the heel portion continuous therewith defines a concavity disposed a distance under the platform.

20. The lower limb prosthesis of claim 19 wherein the ankle portion of the keel is characterized as having a horizontal slot generally below and parallel to the platform and above the arch and continuous with the concavity, wherein the horizontal slot extends a distance from the posterior aspect of the ankle portion towards the anterior aspect of the ankle portion to form an anterior end portion, and wherein the horizontal slot extends the width of the ankle portion.

21. The lower limb prosthesis of claim 20 wherein the anterior end portion of the horizontal slot is substantially circular in longitudinal cross section and has a diameter greater than the width of the horizontal slot.

22. The lower limb prosthesis of claim 20 wherein the means for connecting the leg assembly and the foot includes a vertical throughbore in the ankle portion and a bolt which extends through the throughbore and which threadedly connects to the leg assembly, wherein the central axis of the throughbore is posterior to the apex of the resilient arch in the keel, and wherein the throughbore is intersected by the horizontal slot.

23. The lower limb prosthesis of claim 19 wherein the means for connecting the leg assembly and the foot includes a vertical throughbore in the ankle portion and a bolt which extends through the throughbore and which threadedly connects to the leg assembly, and wherein the central axis of the throughbore is posterior to the apex of the resilient arch in the keel.

24. The lower limb prosthesis of claim 13 wherein the foot is surrounded by a cosmetic covering which is solid except for a cavity positioned under the resilient arch of the keel and extending a distance under the forefoot portion and the heel portion of the keel.

* * * * *

UNITED STATES PATENT AND TRADEMARK OFFICE
CERTIFICATE OF CORRECTION

PATENT NO. : 5,219,365

DATED : June 15, 1993

INVENTOR(S) : John A. Sabolich

It is certified that error appears in the above-identified patent and that said Letters Patent is hereby corrected as shown below:

Column 1, line 43, the word "described" should be -- describes --.

Column 1, line 64, the word "state" should be -- stated --.

Column 2, line 59, after the comma insert the word -- such --.

Column 3, line 23, the word "form" should be -- from --.

Column 4, line 24, the word "FIG." should be -- FIGS.--.

Column 6, line 18, the number "500" should be -- 50 --.

Column 6, line 34, the words "along along" should be -- along almost --.

Column 6, line 47, the word "ha" should be -- has --.

Column 6, line 67, the word "an" should be -- and --.

Column 7, line 32, the word "sol-called" should be -- so-called --.

UNITED STATES PATENT AND TRADEMARK OFFICE
CERTIFICATE OF CORRECTION

PATENT NO. : 5,219,365
DATED : June 15, 1993
INVENTOR(S) : John A. Sabolich

It is certified that error appears in the above-identified patent and that said Letters Patent is hereby corrected as shown below:

Column 8, line 19, the word "and" should be deleted.

Signed and Sealed this

Twenty-second Day of February, 1994

Attest:

BRUCE LEHMAN

*Attesting Officer*  *Commissioner of Patents and Trademarks*